US012433779B2

(12) United States Patent
Hsieh

(10) Patent No.: US 12,433,779 B2
(45) Date of Patent: Oct. 7, 2025

(54) WAIST PROTECTION BELT

(71) Applicant: Homeway Technology Co., Ltd., Tainan (TW)

(72) Inventor: Chin-Hsing Hsieh, Tainan (TW)

(73) Assignee: HOMEWAY TECHNOLOGY CO., LTD., Tainan (TW)

( * ) Notice: Subject to any disclaimer, the term of this patent is extended or adjusted under 35 U.S.C. 154(b) by 290 days.

(21) Appl. No.: 18/318,022

(22) Filed: May 16, 2023

(65) Prior Publication Data

US 2024/0023655 A1 Jan. 25, 2024

(30) Foreign Application Priority Data

Jul. 21, 2022 (TW) ................................ 111207837

(51) Int. Cl.
*A61F 5/02* (2006.01)

(52) U.S. Cl.
CPC .................................. *A61F 5/028* (2013.01)

(58) Field of Classification Search
CPC .......... A61F 5/028; A61F 5/026; A61F 5/024; A61F 5/022; A61F 5/02; A61F 5/37; A61F 5/05808; A61F 5/058
See application file for complete search history.

(56) References Cited

U.S. PATENT DOCUMENTS 5,188,586 A * 2/1993 Castel ................ A41D 13/0525 128/845
5,548,843 A * 8/1996 Chase ................ A41D 13/0531 2/93
2009/0060963 A1 * 3/2009 Hsieh ..................... A01N 25/10 424/404

FOREIGN PATENT DOCUMENTS

| | | | | | |
|---|---|---|---|---|---|
| CN | 108478930 | A | * | 9/2018 | |
| CN | 208192235 | U | * | 12/2018 | |
| CN | 208300998 | U | * | 1/2019 | |
| CN | 208927448 | U | * | 6/2019 | |
| CN | 211158188 | U | * | 8/2020 | |
| CN | 211383488 | U | * | 9/2020 | |
| CN | 115038351 | A | * | 9/2022 | A41D 13/0525 |
| ES | 2288704 | T3 | * | 1/2008 | A62B 25/00 |
| JP | 3896527 | B2 | * | 3/2007 | |
| JP | 3133434 | U | * | 7/2007 | |
| JP | 3155331 | U | * | 11/2009 | |
| JP | 2019163554 | A | * | 9/2019 | |
| JP | 7158823 | B2 | * | 10/2022 | A41B 9/12 |
| KR | 102172812 | B1 | * | 11/2020 | |

* cited by examiner

*Primary Examiner* — Tarla R Patel
(74) *Attorney, Agent, or Firm* — Crowell & Moring LLP

(57) ABSTRACT

The waist protection belt includes a main belt unit and a tightening belt unit. The main belt unit includes a material that releases far infrared radiation and negative ions, and graphene, and that is adapted to be worn around the waist of a user. The tightening belt unit includes a tightening belt member that is elastically stretchable and that includes a middle belt part positioned on the main belt unit, and two side belt parts extending respectively and oppositely from the middle belt part in a left-right direction. The side belt parts are separably connectable to each other so that the tightening belt member surrounds and elastically tightens the main belt unit.

8 Claims, 6 Drawing Sheets

WAIST PROTECTION BELT

CROSS-REFERENCE TO RELATED APPLICATION

This application claims priority to Taiwanese Utility Model Patent Application No. 111207837, filed on Jul. 21, 2022.

FIELD

The disclosure relates to a waist protection belt, and more particularly to a waist protection belt made of graphene.

BACKGROUND

People nowadays using computers and working long hours in an office are prone to lower back pain due to poor posture. For a person experiencing lower back pain, to resolve this problem, one solution is to wear a waist protection belt so as to provide support to his/her waist. Although a conventional waist protection belt provides certain support to the waist, an enhanced waist protection belt offering stronger support and other health benefits may further promote the health and wellbeing of a user.

SUMMARY

Therefore, an object of the disclosure is to provide a waist protection belt that can alleviate at least one of the drawbacks of the prior art.

According to the disclosure, the waist protection belt includes a main belt unit and a tightening belt unit.

The main belt unit includes a material that releases far infrared radiation and negative ions, and graphene, and that is adapted to be worn around waist of a user.

The tightening belt unit includes a tightening belt member that is elastically stretchable and that includes a middle belt part positioned on the main belt unit, and two side belt parts extending respectively and oppositely from the middle belt part in a left-right direction. The side belt parts are separably connectable to each other so that the tightening belt member surrounds and elastically tightens the main belt unit.

BRIEF DESCRIPTION OF THE DRAWINGS

Other features and advantages of the disclosure will become apparent in the following detailed description of the embodiment(s) with reference to the accompanying drawings. It is noted that various features may not be drawn to scale.

DETAILED DESCRIPTION

Figure 1:
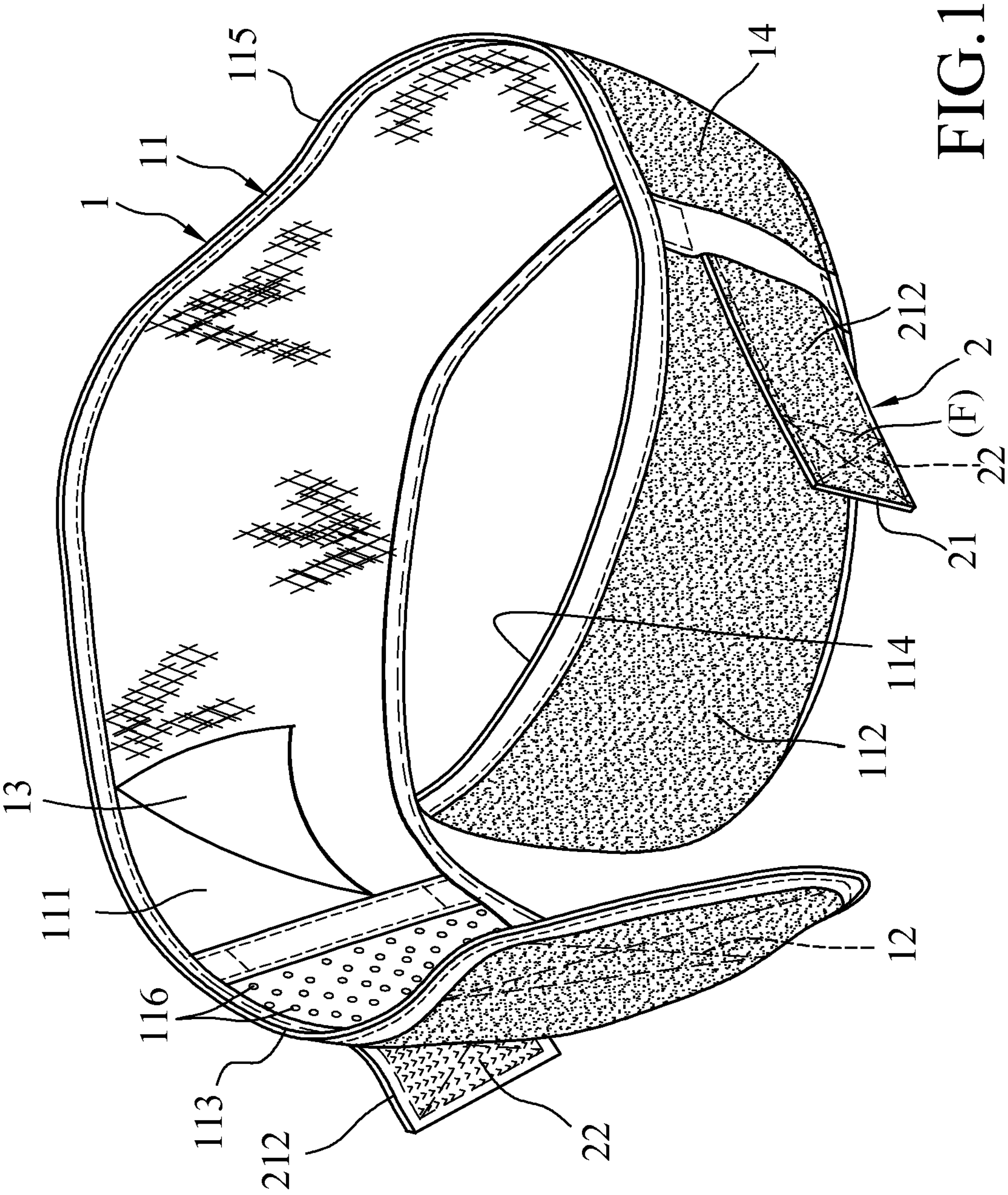
FIG. 1 is a perspective view illustrating an embodiment of a waist protection belt made of graphene according to the disclosure, in which a part of a first sheet is pulled apart and turned outwards from a base sheet so as to partially uncover a first surface of the base sheet.

Before the disclosure is described in greater detail, it should be noted that where considered appropriate, reference numerals or terminal portions of reference numerals have been repeated among the figures to indicate corresponding or analogous elements, which may optionally have similar characteristics.

It should be noted herein that for clarity of description, spatially relative terms such as “top,” “bottom,” “upper,” “lower,” “on,” “above,” “over,” “downwardly,” “upwardly” and the like may be used throughout the disclosure while making reference to the features as illustrated in the drawings. The features may be oriented differently (e.g., rotated 90 degrees or at other orientations) and the spatially relative terms used herein may be interpreted accordingly.

Figure 6:
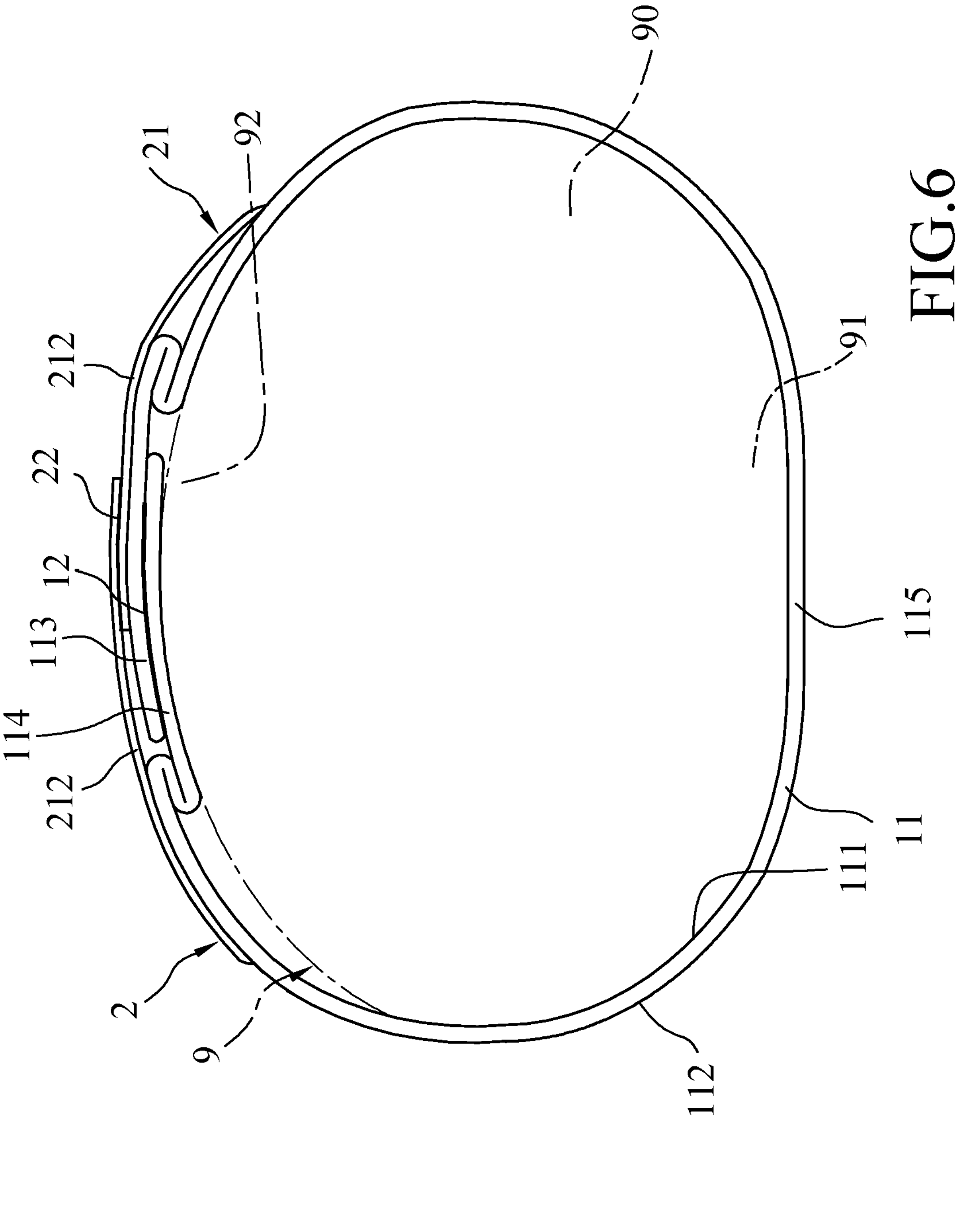
FIG. 6 is a top view, similar to FIG. 5, but illustrating the embodiment of the waist protection belt in a tightening configuration.

Referring to FIGS. 1 to 4, an embodiment a waist protection belt according to the disclosure is provided and is adapted to be worn around the waist 90 of a user 9 (as shown in FIG. 6).

Figure 2:
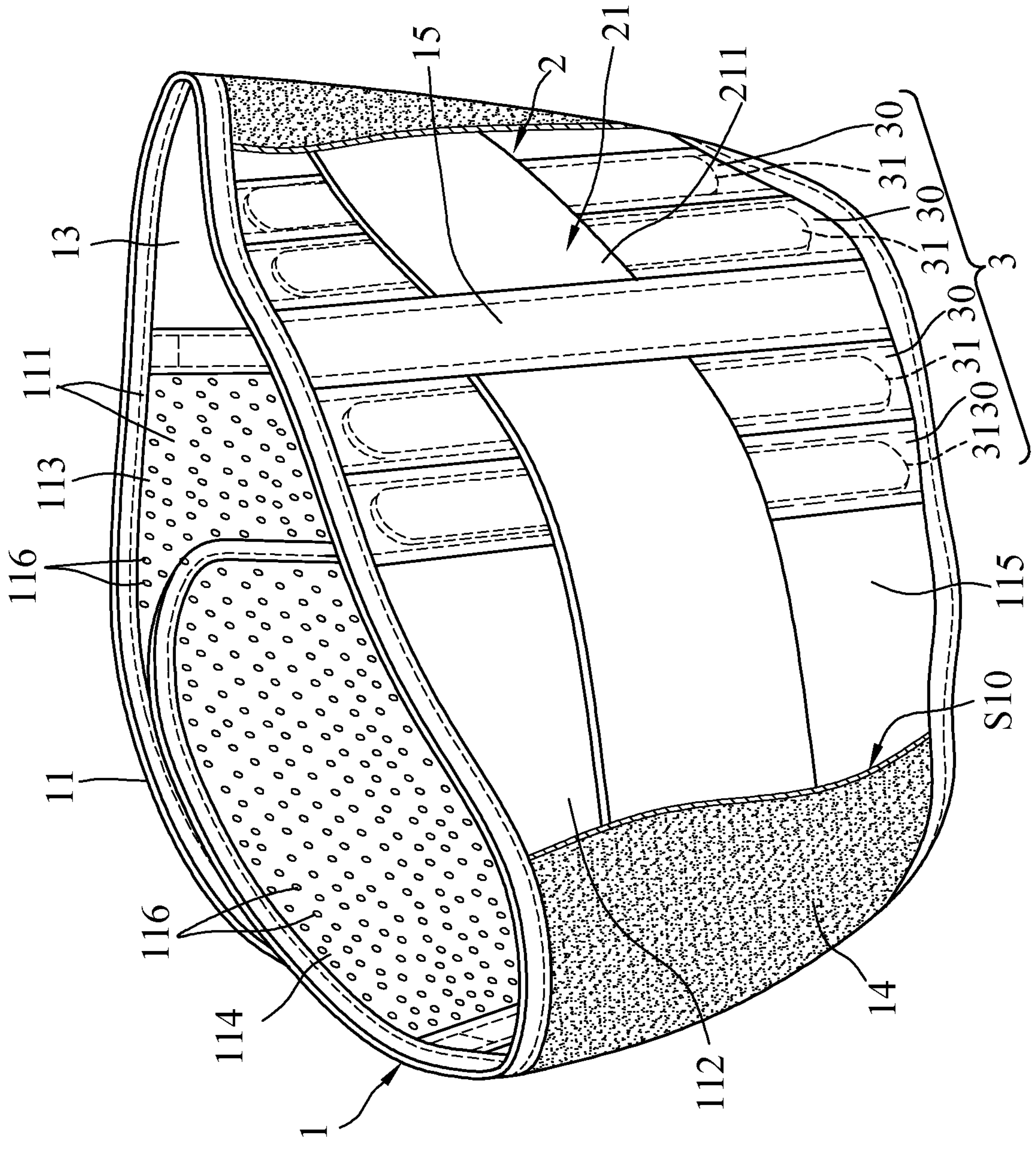
FIG. 2 is a perspective view illustrating a part of a second sheet of the embodiment being removed.
Figure 3:
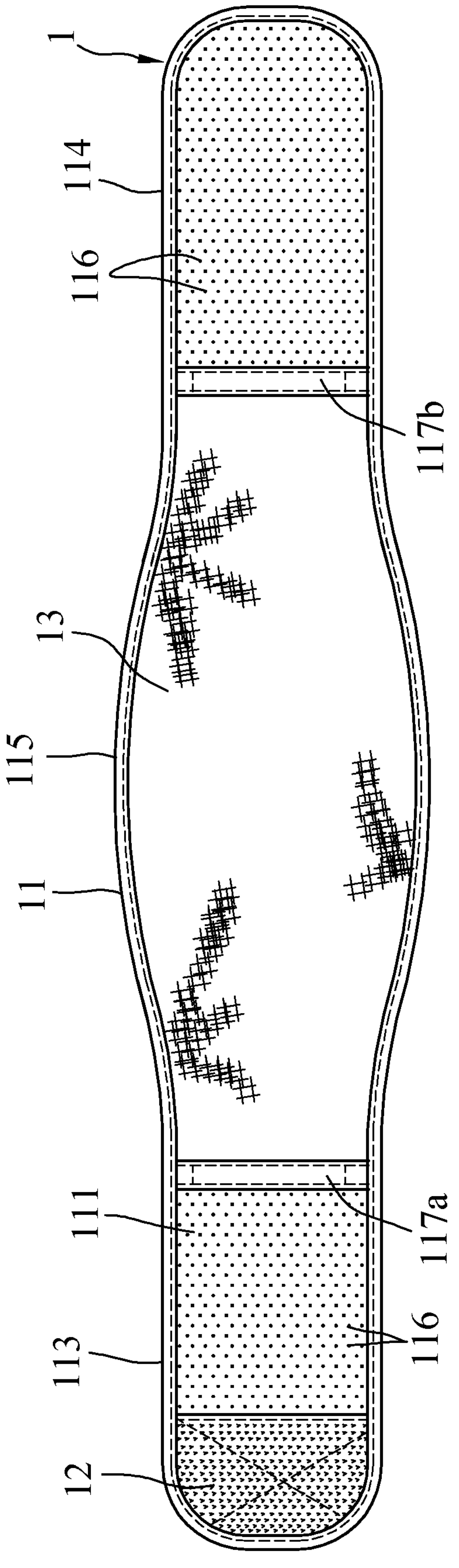
FIG. 3 is a front view illustrating a front side of the embodiment of the waist protection belt facing inwards when being worn by the user.

In this embodiment, the waist protection belt includes a main belt unit 1 that may extend in a left-right direction as shown in FIG. 3 and that may be looped as shown in FIGS. 1 and 2, a tightening belt unit 2 that is positioned on the main belt unit 1, and a supporting unit 3.

The main belt unit 1 includes a base sheet 11 having a first surface 111 and a second surface 112 opposite to the first surface 111, a first fastener strap 12 disposed at one end of the base sheet 11 on the second surface 112, a first sheet 13 disposed on the first surface 111 of the base sheet 11, a second sheet 14 disposed on the second surface 112 of the base sheet 11, and a fixing member 15 sewn to the second surface 112 of the base sheet 11 to fix the tightening belt unit 2 onto the base sheet 11.

The base sheet 11 is made of a material or yarn that releases far infrared radiation and negative ions. In this embodiment, a material that is commercially known as nano germanium yarn and that includes nano germanium is used for making the base sheet 11. By virtue of the base sheet 11 having a nano germanium material, the base sheet 11 may release far infrared radiation and negative ions. Far infrared radiation may induce vibration of water molecules in body cells and blood, thereby stimulating the body cells and their growth, increasing metabolism, improving blood circulation, and discharging body waste and toxins. The negative ions may decompose toxic and harmful substances, and are antibacterial, thereby may eliminate odor and prevent bacteria and mold from growing.

The base sheet 11 includes a first end part 113 and a second end part 114 that are opposite to each other in the left-right direction and that are separably connectable to each other for the user 9 to wear the base sheet 11 around the waist, and an intermediate part 115 that is located between the first end part 113 and the second end part 114 and that is provided for the first sheet 13 to be positioned onto. The first end part 113, the second end part 114, and the intermediate part 115 cooperatively define the first surface 111 and the second surface 112.

The first end part 113 and the second end part 114 are formed with a plurality of ventilation holes 116 on the first surface 111 (see FIG. 3). On the second surface 112, the first end part 113 and the second end part 114 are respectively formed with fiber structures (F) each having fibrous fastener elements that may connect and secure Velcro hooks (see FIG. 4). Since such fiber structures (F) that may connect and secure Velcro hooks is well known in the art, a detailed illustration and numbering in the figures are omitted.

As shown in FIG. 3, the main belt unit 1 further includes a first band 117*a* and a second band 117*b* that extend in an up-down direction on the first surface 111 of the base sheet 11. The first band 117*a* is located where the intermediate part 115 meets the first end part 113, and the second band 117*b* is located where the intermediate part 115 meets the second end part 114. The first sheet 13 has one end fastened, such as by sewing, to the base sheet 11 together with the first band 117*a*, and the other end of the first sheet 13 is fastened, such as by sewing, to the base sheet 11 together with the second band 117*b*.

Figure 4:
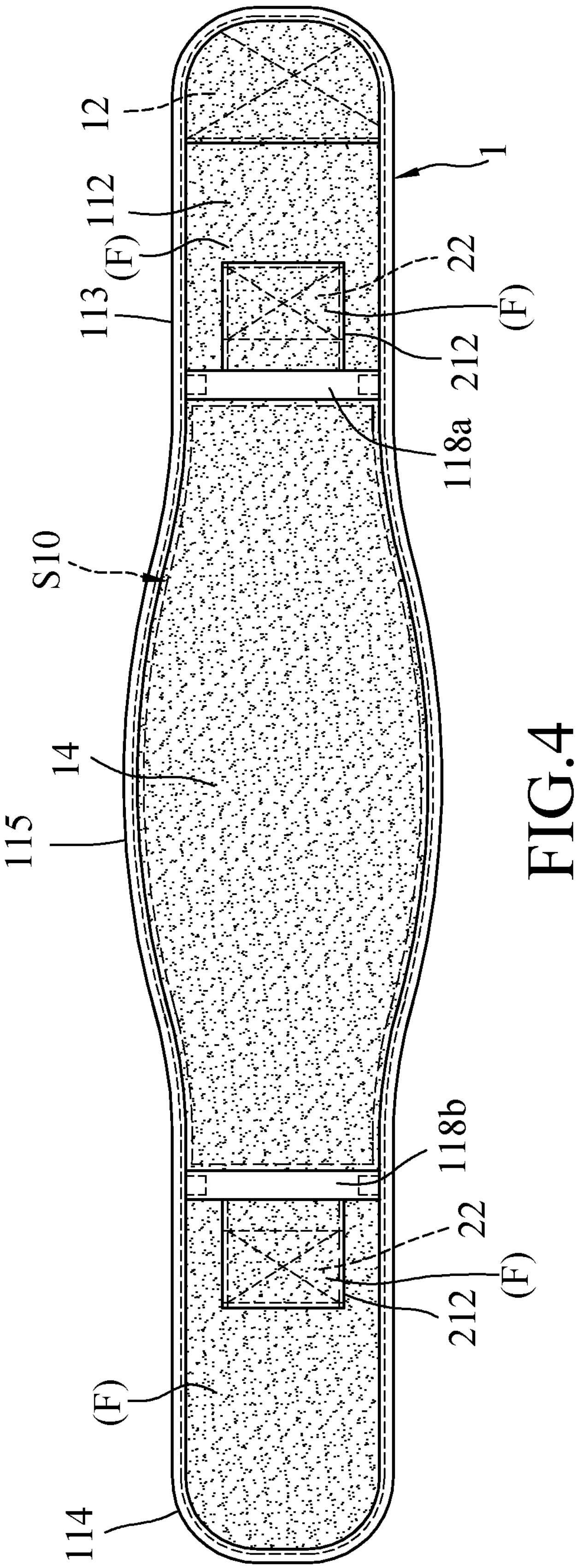
FIG. 4 is a rear view illustrating a rear side of the embodiment of the waist protection belt facing outwards when being worn by the user.

As shown in FIG. 4, the main belt unit 1 further includes a third band 118*a* and a fourth band 118*b* that extend in an up-down direction on the second surface 112 of the base sheet 11. The third band 118*a* is located where the base intermediate part 115 meets the first end part 113, and the fourth band 118*b* is located where the intermediate part 115 meets the second end part 114. The second sheet 14 has one end fastened to (e.g., sewn to) the base sheet 11 together with the third band 118*a*, and the other end of the second sheet 14 is fastened to (e.g., sewn to) the base sheet 11 together with the fourth band 118*b*.

Referring to FIGS. 1 and 4, the first fastener strap 12 is disposed on the first end part 113 and has Velcro hooks that may be connected and secured to the fiber structure (F) of the second end part 114 on the second surface 112.

Apart from having the two ends which are sewn together with the first and second bands 117*a*, 117*b* as described hereinbefore, the first sheet 13 also has its upper and lower ends sewn to the intermediate part 115 at the first surface 111. The first sheet 13 is made of a yarn that includes graphene, for example, a commercially available yarn called LiZi quantum yarn, which is a blend of elastic yarn and peptide yarn. The elastic yarn is blended with graphene. Graphene may produce far infrared radiation, and therefore may also stimulate body cells, improve blood circulation, discharge body waste and toxins, etc. The peptide yarn includes peptide proteins.

Referring back to FIGS. 1, 2 and 4, apart from having the two ends which are sewn together with the second bands 118*a*, 118*b* as described hereinbefore, the second sheet 14 has its upper and lower ends sewn to the intermediate part 115, and covers the intermediate part 115, so that a passage (S10) that extends in the left-right direction is defined between the second sheet 14 and the intermediate part 115. The passage (S10) is opened between upper and lower ends of each of the second bands 118*a*, 118*b*, which are sewn respectively to the upper and lower ends of the second sheet 14, to allow exit of the tightening belt unit 2 from the passage (S10).

The fixing member 15 is strip-shaped and extends in an up-down direction.

The tightening belt unit 2 includes a tightening belt member 21 extending in the left-right direction inside the passage (S10), and two second fastener straps 22 disposed on the tightening belt member 21.

A length of the tightening belt member 21 extending in the left-right direction is shorter than that of the base sheet 11 extending in the left-right direction. The tightening belt member 21 is made of a material that is elastically stretchable, specifically is made of Lycra elastic yarns.

The tightening belt member 21 includes a middle belt part 211 that is positioned on the main belt unit 1 and that is positioned to the intermediate part 115 of the base sheet 11 inside the passage (S10) by the fixing member 15, and two side belt parts 212 that extend respectively and oppositely from the middle belt part 211 in the left-right direction and that protrude outward from the second sheet 14 and the passage (S10). The side belt parts 212 are separably connectable to each other so that the tightening belt member 21 surrounds and elastically tightens the main belt unit 1. The side belt parts 212 of the tightening belt member 21 exit the passage (S10) where the third band 118*a* and the fourth band 118*b* are located.

Referring back to FIGS. 1, 4, each of the side belt parts 212 has a surface that is provided with a fiber structure (F) for connecting and securing Velcro hooks and that faces away from the second surface 112 of the base sheet 11. Since the fiber structure (F) that may connect and secure hooks of Velcro is well known in the art, a detailed illustration and numbering in the figures are omitted.

Each of the second fastener straps 22 has Velcro hooks, and is disposed at a surface of one of the side belt parts 212 that faces towards the second surface 112 of the base sheet 11.

The supporting unit 3 is disposed on the base sheet 11, and includes a plurality of cloth strips 30 sewn to the base sheet 11 and extending in the up-down direction, and a plurality of supporting members 31, each of which extends in the up-down direction and is located between one of the cloth strips 30 and the base sheet 11. The supporting members 31 are divided into groups which are spaced apart from each other in the left-right direction and each of which has a plurality of the supporting members 31. In some embodiments, there may be two groups of the supporting members 31 respectively on two sides of the fixing member 15 in the left-right direction. The supporting members 31 are made of a material that is flexible and resilient, such as polypropylene (PP), so as to provide proper support to the user 9 while being capable of deforming slightly with movement of the user 9.

Figure 5:
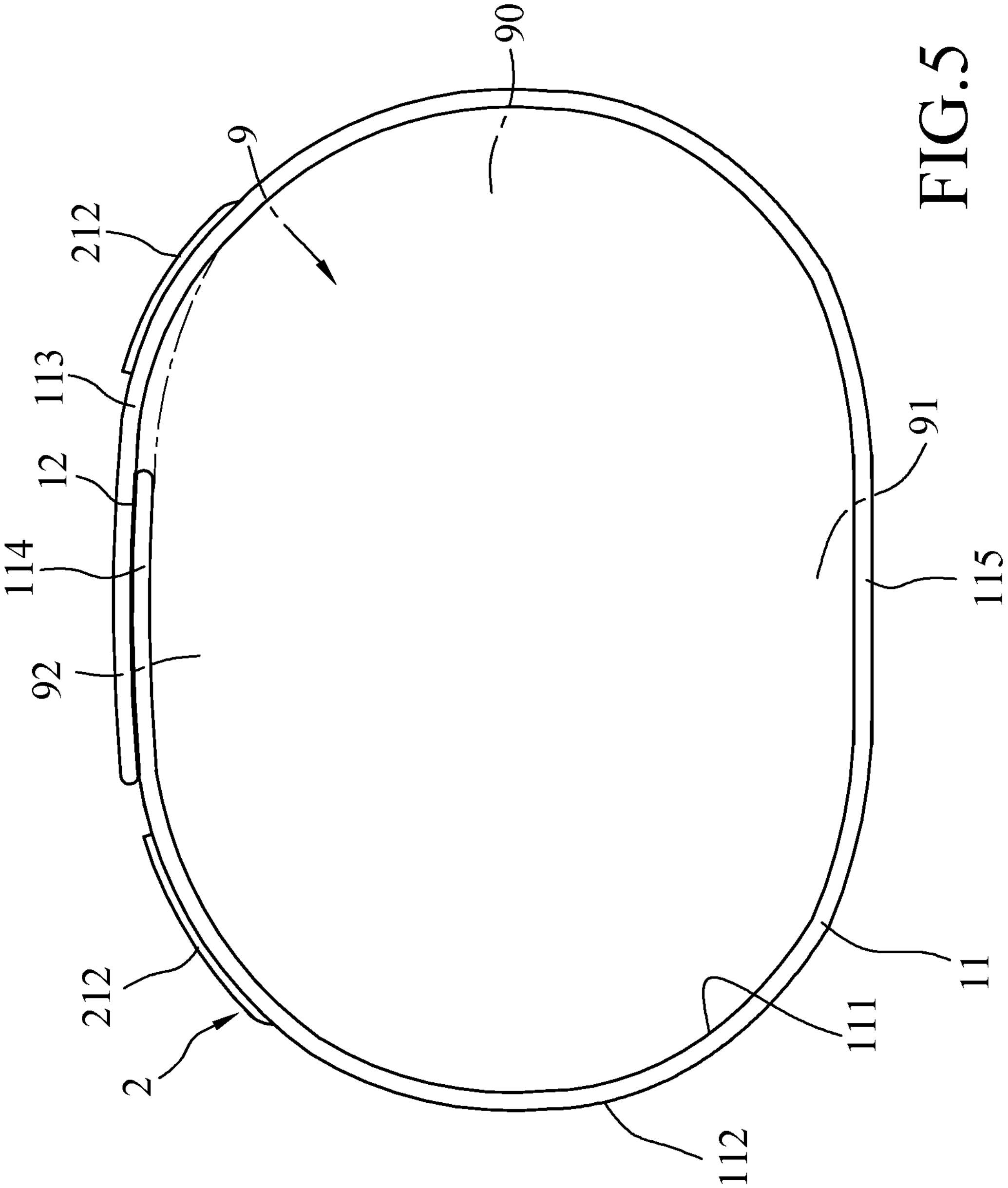
FIG. 5 is a top view illustrating the embodiment of the waist protection belt in an initial wearing configuration, in which an imaginary line represents waist of the user.

Referring to FIGS. 2, 5, and 6, the waist protection belt may be used in the following way: First, the intermediate part 115 is placed behind the lower back 91 of the user 9 as shown in FIG. 5 with the first surface 111 facing the user 9. Next, the first end part 113 and the second end part 114 of the base sheet 11 are drawn to the abdomen 92 of the user 9, so that the first fastener strap 12 at the first end part 113 binds with the second end part 114, thereby overlapping the first end part 113 and the second end part 114. In this way, the waist protection belt is looped and worn around the waist 90 of the user 9 as shown in FIG. 5.

The waist protection belt of the embodiment having an initial wearing configuration shown in FIG. 5 may be changed to a tightening configuration shown in FIG. 6. In FIG. 5, due to the length of the tightening belt member 21 being shorter than that of the base sheet 11 extending in the left-right direction, the two side belt parts 212 of the tightening belt member 21 are spaced apart from each other in the left-right direction.

By pulling the side belt parts 212 toward each other and to the abdomen 92 of the user 9, the tightening belt member 21 is elastically stretched, and tightens and presses the base sheet 11 against the user 9. When the second fastener strap 22 on one of the side belt parts 212 is placed over and pressed against the other one of the side belt parts 212, the two side belt parts 212 are secured together.

In the tightening configuration, due to the tightening belt member 21 being stretched and deformed, the tightening belt member 21 stores an elastic force that makes the base sheet 11 tighten the waist 90 of the user 9 even more, so the tightening belt member 21 may further support the waist 90 of the user 9 in this embodiment. In addition, the supporting members 31 of the supporting unit 3 are located on the left and right sides of the fixing member 15, and the supporting members 31 extend in the up-down direction same as the direction in which the spine of the user 9 extends, thereby further supporting the muscles on both sides of the spine and providing a better overall support.

Another feature of the present disclosure lies in that the base sheet 11 includes nano germanium, and that the main belt unit 1 includes a material that releases far infrared radiation and negative ions, and graphene, so the present embodiment may protect the waist 90 of the user 9 while stimulating the body cells and blood circulation of the waist 90 of the user 9, thereby further improving health of the user 9.

Yet another feature of the present disclosure lies in the fixing members 15 extending in a direction perpendicular to a direction in which the tightening belt member 21 extends, so when the tightening belt member 21 is drawn in the left-right direction, the fixing members 15 may provide an even and stable fixing force.

In summary, the tightening belt member 21 is capable of further elastically tightening the base sheet 11, thereby providing better support. The far infrared radiation and negative ions released by the main belt unit 1 may further promote the health of the waist 90 of the user 9, and so the purpose of this disclosure is achieved.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects; such does not mean that every one of these features needs to be practiced with the presence of all the other features. In other words, in any described embodiment, when implementation of one or more features or specific details does not affect implementation of another one or more features or specific details, said one or more features may be singled out and practiced alone without said another one or more features or specific details. It should be further noted that one or more features or specific details from one embodiment may be practiced together with one or more features or specific details from another embodiment, where appropriate, in the practice of the disclosure.

While the disclosure has been described in connection with what is(are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A waist protection belt comprising:

a main belt unit including a material that releases far infrared radiation and negative ions, and graphene, and that is adapted to be worn around waist of a user; and a tightening belt unit including a tightening belt member that is elastically stretchable and that includes a middle belt part positioned on said main belt unit, and two side belt parts extending respectively and oppositely from said middle belt part in a left-right direction, said side belt parts being separably connectable to each other so that said tightening belt member surrounds and elastically tightens said main belt unit, wherein said main belt unit includes a base sheet, and a first sheet and a second sheet respectively disposed oppositely on a first surface and a second surface of said base sheet, said base sheet being made of said material that releases far infrared radiation and negative ions and including a first end part and a second end part that are opposite to each other in the left-right direction and that are separably connectable to each other for the user to wear said base sheet around the waist, said first sheet being made of a material that includes graphene, said second sheet and said base sheet cooperating to define a passage that extends in the left-right direction, said middle belt part of said tightening belt being positioned to said base sheet inside said passage, said side belt parts extending oppositely in the left-right direction from said middle belt part and protruding outward from said second sheet and said passage, wherein said base sheet further includes an intermediate part disposed between said first end part and said second end part, said passage being formed between said second sheet and said intermediate part of said base sheet, said middle belt part of said tightening belt member being positioned to said intermediate part of said base sheet inside said passage, and wherein said main belt unit further includes a third band and a fourth band that extend in an up-down direction on said second surface of said base sheet, said third band being located where said base intermediate part meets said first end part, said fourth band being located where said base intermediate part meets said second end part, said second sheet having one end fastened to said base sheet together with said third band, the other end of said second sheet being fastened to said base sheet together with said fourth band, said side belt parts of said tightening belt member exiting said passage where said third band and said fourth band are located.

2. The waist protection belt as claimed in claim 1, wherein said base sheet is made of yarns including said material that releases far infrared radiation and negative ions, said first sheet being made of yarns that include graphene.

3. The waist protection belt as claimed in claim 1, wherein said main belt unit further includes a fixing member that fixes said middle belt part of said tightening belt member onto said base sheet.

4. The waist protection belt as claimed in claim 3, wherein said fixing member is strip-shaped and extends in an up-down direction.

5. The waist protection belt as claimed in claim 1 further comprising a supporting unit disposed on said base sheet.

6. The waist protection belt as claimed in claim 5, wherein said supporting unit includes a plurality of cloth strips sewn to said base sheet and extending in an up-down direction, and a plurality of supporting members, each of which extends in the up-down direction and is located between one of said cloth strips and said base sheet, said supporting members being divided into groups which are spaced apart from each other in the left-right direction and each of which has a plurality of said supporting members.

7. The waist protection belt as claimed in claim 1, wherein a length of said tightening belt member extending in the left-right direction is shorter than that of said base sheet extending in the left-right direction.

8. The waist protection belt as claimed in claim 1, wherein said main belt unit further includes a first band and a second band that extend in an up-down direction on said first surface of said base sheet, said first band being located where said base intermediate part meets said first end part, said second band being located where said base intermediate part meets said second end part, said first sheet having one end fastened to said base sheet together with said first band, the other end of said first sheet being fastened to said base sheet together with said second band.

* * * * *